United States Patent [19]

Belletire

[11] 4,210,663
[45] Jul. 1, 1980

[54] HALOGEN SUBSTITUTED BENZOPYRAN- AND BENZOTHIOPYRAN-4-CARBOXYLIC ACIDS

[75] Inventor: John L. Belletire, Madison, Wis.

[73] Assignee: Pfizer Inc., New York, N.Y.

[21] Appl. No.: 959,023

[22] Filed: Nov. 8, 1978

[51] Int. Cl.$^2$ .................... A61K 31/38; A61K 31/35; C07D 311/04; C07D 335/06
[52] U.S. Cl. ........................ 424/275; 549/23; 260/345.2; 260/345.5; 424/283
[58] Field of Search .......... 260/327 TH, 345.2, 345.5; 424/275, 283; 549/23

[56] References Cited
PUBLICATIONS

Ann. Chim. Paris, No. 3, 179 (1968) (Maitte).
Chem. Abs. 75 98400b (1971) (Witiak et al.).
Chem. Abs. 82 57517w (1975) (Zaugg et al.).

Primary Examiner—Henry R. Jiles
Assistant Examiner—Robert C. Whittenbaugh

Attorney, Agent, or Firm—Francis X. Murphy; Charles J. Knuth; Peter C. Richardson

[57] ABSTRACT

Novel halogen-substituted benzopyran-4-carboxylic acids, benzothiopyran-4-carboxylic acids and derivatives thereof useful as aldose reductase inhibitors and as therapeutic agents for the treatment of chronic diabetic complications are disclosed. Specific compounds disclosed include 6-phenyl-8-chloro-3,4-dihydro-2H-1-benzopyran-4-carboxylic acid, 6,7-dichloro-3,4-dihydrobenzothiopyran-4-carboxylic acid, 6-chloro-8-methyl-3,4-dihydro-2H-1-benzopyran-4-carboxylic acid, 6,8-dichloro-3,4-dihydro-2H-1-benzopyran-4-carboxylic acid, 6-fluoro-3,4-dihydro-2H-1-benzopyran-4-carboxylic acid, 6-chloro-3,4-dihydro-2H-1-benzopyran-4-carboxylic acid, 6-chloro-dihydro-2H-naphtho[1,2-b]pyran-4-carboxylic acid, 6-chloro-3,4-dihydro-2H-1-benzothiopyran-4-carboxylic acid and 6-chloro-3,4-dihydro-2H-1-benzopyran-4-acetic acid. Also disclosed are pharmaceutical compositions containing the novel compounds and a method of using the novel compounds for the treatment of chronic diabetic complications.

25 Claims, No Drawings

HALOGEN SUBSTITUTED BENZOPYRAN- AND BENZOTHIOPYRAN-4-CARBOXYLIC ACIDS

BACKGROUND OF THE INVENTION

This invention relates to novel halogen-substituted benzopyran- and benzothiopyran-4-carboyxlic acids and derivatives thereof useful in the treatment of certain chronic complications arising from diabetes mellitus, such as diabetic cataracts and neuropathy, to pharmaceutical compositions containing such compounds and to a method of using the compounds.

In the past various attempts have been made to obtain new and more effective oral anti-diabetic agents. Generally, these efforts have involved synthesis of new organic compounds, particularly sulfonylureas, and determination of their ability to substantially lower blood sugar levels when administered orally. However, little is known about the effect of organic compounds in preventing or alleviating chronic complications of diabetes, such as diabetic cataracts, neuropathy and retinopathy. U.S. Pat. No. 3,821,383 discloses aldose reductase inhibitors like 1,3-dioxo-1H-benz[d,e]-isoquinoline-2(3H)-acetic acid and derivatives thereof to be useful for the treatment of these conditions. Such aldose reductase inhibitors function by inhibiting the activity of the enzyme aldose reductase, which is primarily responsible for regulating the reduction of aldoses, such as glucose and galactose to the corresponding polyols, such as sorbitol and galacticol, in humans and other animals. In this way, unwanted accumulations of galacticol in the lens of galactosemic subjects and of sorbitol in the lens, peripheral nervous cord and kidney of various diabetic subjects are prevented or reduced. Accordingly, such compounds are of therapeutic value as aldose reductase inhibitors for controlling certain chronic diabetic complications, including those of an ocular nature, since it is known in the art that the presence of polyols in the lens of the eye leads to cataract formation, with a concomitant loss of lens clarity.

SUMMARY OF THE INVENTION

The present invention relates to novel aldose reductase inhibitors useful as therapeutic agents for preventing or alleviating chronic diabetic complications. Specifically, the compounds of the present invention are novel halogen substituted benzopyran- and benzothiopyran-4-carboxylic acids and derivatives thereof having the formula

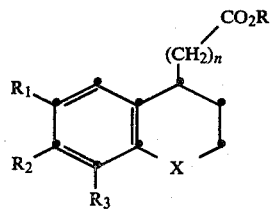

and the pharmaceutically acceptable salts thereof, wherein

X is selected from the group consisting of O, S, SO, and $SO_2$; n is zero or one;

R is selected from the group consisting of hydrogen and alkyl of 1 to 4 carbon atoms;

$R_1$ is selected from the group consisting of hydrogen, chloro, bromo, fluoro, and phenyl;

$R_2$ and $R_3$, when taken individually are each selected from hydrogen, alkyl of 1 to 3 carbon atoms, chloro, bromo, and fluoro; and when taken together $R_2$, $R_3$ and the carbon atoms to which they are connected form a fused benzene ring; with the proviso that at least one of $R_1$, $R_2$ and $R_3$ is selected from the group consisting of chloro, bromo and fluoro.

One group of compounds of interest is that wherein X is oxygen. $R_1$ is preferably chloro, fluoro or phenyl, R is preferably hydrogen and preferred groups for $R_2$ and $R_3$ are hydrogen, methyl, chloro and, taken together, a fused benzene ring. Especially preferred compounds are those where n is zero, such as 6-chloro-8-methyl-3,4-dihydro-2H-1-benzopyran-4-carboxylic acid, 6,8-dichloro-3,4-dihydro-2H-1benzopyran-4-carboxylic acid, 6-chloro-3,4-dihydro-2H-1-benzopyran-4-carboxylic acid, 6-chloro-3,4-dihydro-2H-naptho[1,2-b]pyran-4-carboxylic acid, 6-phenyl-8-chloro-3,4-dihydro-2H-1-benzopyran-4-carboxylic acid and 6-fluoro-3,4-dihydro-2H-1-benzopyran-4-carboxylic acid. A preferred compound when n is one is 6-chloro-3,4-dihydro-2H-benzopyran-4-acetic acid.

A further group of compounds of interest is that wherein X is sulphur. Preferably, $R_1$ is chloro or fluoro, R is hydrogen, $R_2$ and $R_3$ are hydrogen, methyl or chloro. When n is zero preferred compounds include 6,7-dichloro-3,4-dihydro-2H-1-benzothiopyran-4-carboxylic acid and 6-chloro-3,4-dihydro-2H-1-benzothiopyran-4-carboxylic acid.

The present invention further comprises a novel method for the treatment of a diabetic host to prevent or alleviate diabetes-associated complications, such as cataracts, neuopathy or retinopathy, which method comprises administering to the host an effective amount of a compound of Formula I. Also embraced by the present invention are pharmaceutical compositions comprising a pharmaceutically-acceptable carrier and a compound of Formula I in an amount effective to prevent or alleviate diabetes-associated complications, such as cataracts, neuopathy or retinopathy.

DETAILED DESCRIPTION OF THE INVENTION

The novel compounds of Formula I are readily prepared from the corresponding ketones of Formula II

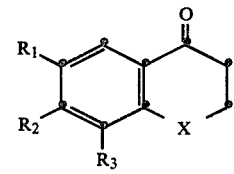

wherein $R_1$, $R_2$, $R_3$ and X are as previously defined. The ketone starting materials are commercially available or may be readily synthesized by reactions known in the art. For example, the ketones may be prepared from an appropriately ($R_1$, $R_2$, $R_3$)-substituted phenol or thiophenol by reaction with acrylonitrile in the presence of a strong base for example benzyltrimethylammonium hydroxide (Triton B), generally in excess acrylonitrile at reflux temperature. The resulting nitrile is hydrolyzed by heating with an acid such as hydrochloric acid, formic acid and the like, to form the corresponding 3-($R_1$, $R_2$, $R_3$-substituted-phenoxy)-propionic acid, or the thio analog thereof. The acid may also be formed by the reaction of the ($R_1$ $R_2$ $R_3$)-substituted phenol or thiophenol with 3-bromo-propionic acid in the presence of a base, such as an alkali metal hydroxide, at a temperature of about 50° to 100° C. The ketone is formed by cyclization of the 3-($R_1R_2R_3$)-substituted-phenoxy)-propionic acid by heating in the presence of a strong acid such as polyphosphoric acid or sulfuric acid.

Compounds of Formula I wherein n is zero are readily formed from the appropriately substituted ketone of Formula II by reaction wth a trialkylsilyl cyanide to form the 4-cyano-4-trialkylsilyloxy-derivative, followed by reductive hydrolysis to the desired acid. A preferred trialkylsilyl cyanide for use in this reaction is trimethylsilyl cyanide, although other lower trialkylsilyl cyanides having from 1 to 4 carbon atoms in each alkyl group may be employed. The reaction of the ketone and the trialkylsilyl cyanide is conducted in the presence of a Lewis acid catalyst, such as a zinc halide, aluminum halide or boron trifluoride, with zinc iodide being a preferred catalyst. The reaction is generally conducted at temperatures in the range of about 0° to 50° C., preferably about 0° to 20° C., either neat or in an inert organic solvent, typically an ether such as diethyl ether, dimethoxyethane, tetrahydrofuran, dioxane and the like. Preferably, the reaction is conducted in a inert atmosphere, for example under nitrogen. The 4-cyano-4-trialkylsilyloxy-derivative is then converted to the desired acid by heating with a stannous halide, such as stannous chloride dihydrate, in concentrated acid such as a mixture of glacial acetic acid and hydrochloric acid. The reaction is conducted at a temperature of about 100° to 200° C., preferably at reflux temperature, reaction generally being substantially complete in times of about 12 to 72 hours. The acids formed in the above described reaction are readily converted to the corresponding lower alkyl esters by conventional routes, for example by heating with the appropriate alkanol having from 1 to 4 carbon atoms in the presence of an acid catalyst, or by forming the corresponding acid chloride followed by reaction with the appropriate alcohol.

Compounds of Formula I wherein n is one are prepared from the ketones of Formula II by the Wittig reaction with a trialkyl phosphonate ester, such as trimethyl phosphonoacetate, in the presence of a base, such as an alkali metal hydride, for example sodium hydride. The reaction is generally conducted at about 0° to 50° C., preferably about 10° to 30° C., in a dry inert organic solvent such as tetrahydrofuran, dimethoxyethane, dioxane and the like. The olefinic ester produced by this reaction is then reduced, for example with hydrogen in the presence of a noble metal catalyst, preferably palladium on carbon. The reduction is conducted in an inert solvent such as ethyl acetate. The compound of Formula I where n is one is obtained as the corresponding alkyl ester, which can be converted to the acid by hydrolysis in the presence of a base, such as an alkali metal hydroxide, alkoxide or carbonate. If desired, the acid may be converted to esters having other R groups by conventional esterification methods.

Compounds of Formula I wherein X is SO or $SO_2$ may be prepared from the corresponding compounds wherein X is sulfur by conventional oxidation methods. Thus, for example, oxidation of compounds wherein X is sulfur with an alkali metal periodate, or with one equivalent of a peroxy acid results in compounds wherein X is SO. Oxidation with two equivalents of a peroxy acid may be employed to form those compounds wherein X is $SO_2$.

In the above procedures, the halogen substituent at at least one of the $R_1$, $R_2$ or $R_3$ position is preferably present in the ketone starting material of Formula II. However, it is also possible to introduce such substituents by reaction of the unsubstituted compounds of Formula I (i.e. where $R_1$, $R_2$ and $R_3$ are hydrogen) using direct halogenation methods well known in the art. Other desired substituents for $R_1$, $R_2$ and $R_3$ may likewise be introduced by reaction of the unsubstituted compounds using appropriate conventional reagents and methods.

Pharmaceutically acceptable salts can be readily prepared from compounds of Formula I wherein R is hydrogen by conventional methods. Thus, these salts may be readily prepared by treating the halogen substituted benzopyran- or benzo-thiopyran-4-carboxylic acids with an aqueous solution of the desired pharmaceutically acceptable cations, for example a solution of the hydroxide or carbonate, and evaporating the resulting solution to dryness, preferably under reduced pressure. Alternatively, a lower alknol solution of the carboxylic acid of Formula I may be mixed with an alkoxide of the desired metal and the solution evaporated to dryness. Suitable pharmaceutically acceptable salts include, but are not limited to, those having potassium, sodium, ammonium, calcium, or magnesium as the cation.

The novel compounds of Formula I are useful as aldose reductase inhibitors and as such are of therapeutic value in the treatment of chronic complications of diabetes, such as cataracts, retinopathy and neuropathy. As used in the claims and specification hereof, treatment is meant to include both prevention or alleviation of such conditions. The compounds may be administered to a subject in need of treatment by a variety of conventional routes of administration, including orally and parenterally. In general these compounds will be administered at dosages between 1 and 250 mg./kg. body weight of the subject to be treated per day. However, some variation in dosage will necessarily occur depending on the condition of the subject being treated and the physician will, in any event, determine the appropriate dose for the individual subject.

The compounds may be administered alone or in combination with pharmaceutically acceptable carriers, in either single or multiple doses. Suitable pharmaceutical carriers include inert solid diluents or fillers, sterile aqueous solutions and various non-toxic organic solvents. The pharmaceutical compositions formed by combining the novel benzopyran- or benzothiopyran-4-carboxylic acids or derivatives thereof of Formula I and the pharmaceutically acceptable carrier are then readily administered in a variety of dosage forms such as tablets, powders, lozenges, syrups, injectable solutions and the like. These pharmaceutical compositions can, if desired, contain additional ingredients such as flavorings, binders, excipients and the like. Thus, for oral administration, tablets containing various excipients such as sodium citrate, calcium carbonate and calcium phosphate may be employed along with various disintegrants such as starch and potato or tapioca starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tableting purposes. Solid compositions of a similar type may also be employed as fillers in soft and hard-filled gelatin capsules; preferred materials for this include lactose or milk sugar and high molecular weight polethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerine and combinations thereof.

For parenteral administration, solutions of the benzopyran-or benzothiopyran-4-carboxylic acid or derivatives thereof of Formula I in sesame or peanut oil or in aqueous propylene glycol may be employed, as well as sterile aqueous solution of the corresponding water-soluble alkaline metal or alkaline earth metal salts previously described. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal injection purposes. In this connection, the sterile aqueous media employed are all readily obtainable by standard techniques well known to those skilled in the art. Additionally, it is also possible to administer the compounds of Formula I topically by use of an appropriate opthalmic solution which may be administered dropwise to the eye.

The activity of the compounds of the present invention as agents for the control of chronic diabetic complications may be determined by a number of standard biological or pharmacological tests. Suitable tests include (1) measuring their ability to inhibit the enzyme activity of isolated aldose reductase; (2) measuring their ability to reduce or inhibit sorbitol accumulation in the sciatic nerve of acutely streptozotocinized (i.e. diabetic) rats; (3) measuring their ability to reverse already-elevated sorbitol levels in the sciatic nerve and lens of chronic streptozotocin-induced diabetic rats; (4) measuring their ability to prevent or inhibit galactitol formation in the lens of acutely galactosemic rats; and (5) measuring their ability to delay cataract formation and reduce the severity of lens opacities in chronic galactosemic rats.

The present invention is illustrated by the following examples. It will be understood, however, that the invention is not limited to the specific details of these examples.

EXAMPLE 1

To a 500 ml. single neck reaction flask equipped with a magnetic stirrer, a 250 ml. pressure equalizing addition funnel, and a nitrogen inlet was added 6-phenyl-8-chloro-3,4-dihydro-2H-1-benzopyran-4-one (5.02 g) and anhydrous zinc iodide (0.50 g.). The addition funnel was charged with trimethylsilyl cyanide (Silar, 10 ml.) and the reaction apparatus flushed with dry nitrogen. With vigorous stirring the trimethylsilyl cyanide was added over a 15 minutes period, causing a modest exotherm. The reaction mixture was stirred under nitrogen at room temperature for 48 hours. The reaction mixture was diluted with chloroform (500 ml.), the organic layer washed 3 times with saturated sodium bicarbonate, and dried over magnesium sulfate. Filtration and removal of volatiles gave 6-phenyl-8-chloro-4-cyano-4-trimethylsilyloxy-3,4-dihydro-2H-1-benzopyran (5.5 g.). Recrystallization from cyclohexane gave 1.5 g., of product, m.p. 99°–100° C.

Analytical: Calcd: C, 63.76; H, 5.63; Cl, 9.90; N, 3.91 (%). Found: C, 63.88; H, 5.59; Cl, 10.17, N, 3.84 (%).

EXAMPLE 2

To a 500 ml. single neck reaction flask equipped with a magnetic stirrer, reflux condenser, and nitrogen inlet was added 6-phenyl-8-chloro-4-cyano-4-trimethylsilyloxy-3,4-dihydro-2H-1-benzopyran (3.0 g.). In one portion was added stannous chloride dihydrate (15 g.) followed by glacial acetic acid (20 ml.) and concentrated hydrochloric acid (20 ml.). The reaction flask was immediately flushed with nitrogen and plunged into a preheated (140° C.) oil bath. With vigorous stirring the reaction mixture was heated at reflux for 65 hrs., cooled to room temperature, diluted with 500 ml. chloroform, the layers separated, and the aqueous layers again saturated with chloroform. The combined organic layers were extracted with three 150 ml. portions of 2 N aqueous potassium hydroxide, and the combined basic aqueous layers back-extracted with one 150 ml. portion of ether. Acidification of the basic aqueous layer with ice bath cooling, extraction with three 250 ml. portions of chloroform, drying of the combined organic layers over magnesium sulfate, filtration, and removal of the volatiles afforded 6-phenyl-8-chloro-3,4-dihydro-2H-1-benzopyran-4-carboxylic acid. Filtration of a chloroform solution of the acid through 400 ml. of silica gel (EM Reagents, 70–230 mesh) with elution by three liters of chloroform removes a small amount of an -hydroxy acid impurity. Recrystallization from cyclohexane yielded 0.93 g. (38%) of the acid, m.p. 187°–188° C.

Analytical: Calcd: C, 66.56; H, 4.54; Cl, 12.28 (%). Found: C, 66.24; H, 4.55; Cl, 12.14 (%).
m/e: 288

EXAMPLE 3

Following the procedure of Example 1, 6,7-dichloro-3,4-dihydro-2H-1-benzothiopyran-4-one (8.0 g.), trimethylsilyl cyanide (40 ml) and zinc iodide (0.5 g) were reacted to give 6,7-dichloro-4-cyano-4-trimethylsilyloxy-3,4-dihydro-2H-1-benzothiopyran. Filtration and chromatography on silica gel (200 ml.) eluted by 1:1 chloroform:hexane yielded 7.5 g. (66%) of the desired product.

EXAMPLE 4

Following the procedure of Example 2, 6,7-dichloro-4-cyano-4-trimethylsilyloxy-3,4-dihydro-2H-1-benzothiopyran (7.5 g.) and stannous chloride dihydride (30 g.) were reacted in glacial acetic acid (30 ml.) and concentrated hydrochloric acid (30 ml.) to form 6,7-dichloro-3,4-dihydro-2H-1-benzothiopyran-4-carboxylic acid.

Recrystallization from benzene and hexane gave 1.88 g. (32%) of product, m.p. 157°–161° C. (Sublimed).

Analytical: Calcd: C, 45.64; H, 3.06; S, 12.18; Cl, 26.95 (%). Found: C, 45.72; H, 3.00; S, 12.28; Cl. 26.60 (%).

EXAMPLE 5

Following the procedure of Example 1, 6-chloro-8-methyl-3,4-dihydro-2H-1-benzopyran-4-one (5.0 g.), trimethylsilylcyanide (10 ml) and zinc iodide (0.35 g.) were reacted to form 6-chloro-8-methyl-4-cyano-4-trimethylsilyloxy-3,4-dihydro-2H-1-benzopyran. Filtration and chromatography over silica gel (200 ml.) eluted with chloroform:hexane (1:1) yielded 3.3 g. of product.

EXAMPLE 6

Following the procedure of Example 2, 6-chloro-8-methyl-4-cyano-4-trimethylsilyloxy-3,4-dihydro-2H-1-benzopyran (3.1 g.), and stannous chloride dihydrate (12.0 g.) were reacted in glacial acetic acid (25 ml.) and concentrated hydrochloric acid (25 ml.) to form 6-chloro-8-methyl-3,4-dihydro-2H-1-benzopyran-4-carboxylic acid. Recrystallization from hexane yielded 1.67 g. of product, m.p. 95°-96° C.

Analytical: Calcd. C, 58.29; H, 4.89 (%). Found: C, 57.92; H, 4.81 (%).

m/e: 226.

EXAMPLE 7

Following the procedure of Example 1, 6,8-dichloro-3,4-dihydro-2H-1-benzopyran-4-one (6.2 g.), trimethylsilyl cyanide (20 ml.) and zinc iodide (0.41 g.) were reacted in ether (20 ml.) to form 6,8-dichloro-4-cyano-4-trimethylsilyloxy-3,4-dihydro-2H-1-benzopyran. Recrystallization from aqueous isopropanol yielded 6.3 g. of product, m.p. 84°-85° C.

Analytical: Calcd: C, 49.37; H, 4.78; N, 4.43 (%). Found: C, 49.48; H, 4.64; N, 4.53 (%).

m/e: 315, 317, 319.

EXAMPLE 8

Following the procedure of Example 2, 6,8-dichloro-4-cyano-4-trimethylsilyloxy-3,4-dihydro-2H-1-benzopyran (3.0 g.) and stannous chloride dihydrate (15.0 g.) were reacted in glacial acetic acid (25 ml.) and concentrated hydrochloric acid (25 ml.) to form 6,8-dichloro-3,4-dihydro-2H-1-benzopyran-4-carboxylic acid. Recrystallization from cyclohexane yielded 1.33 g. of product, m.p. 124.5°-126° C.

Analytical: Calcd: C, 48.61; H, 3.26 (%). Found: C, 48.52; H, 3.27 (%).

m/e: 246, 248, 250.

EXAMPLE 9

Following the procedure of Example 1, 6-fluoro-3,4-dihydro-2H-1-benzopyran-4-one (3.74 g.), trimethylsilyl cyanide (10 ml.) and zinc iodide (0.43 g.) were reacted to form 6-fluoro-4-cyano-4-trimethylsilyloxy-3,4-dihydro-2H-1-benzopyran. Filtration and chromatography on silica gel (150 ml.) eluted with chloroform:hexane (1:1) yielded 5.0 g. of product.

EXAMPLE 10

Following the procedure of Example 2, 6-fluoro-4-cyano-4-trimethylsilyloxy-3,4-dihydro-2H-1-benzopyran (4.72 g.) and stannous chloride dihydrate (25 g.) were reacted in glacial accetic acid (25 ml.) and concentrated hydrochloric acid (25 ml.) to form 6-fluoro-3,4-dihydro-2H-1-benzopyran-4-carboxylic acid. Recrystallization from ethyl acetate:cyclohexane yielded 2.60 g. of product, m.p. 118°-119° C.

Analytical: Calcd: C, 61.22; H, 4.62 (%). Found: C, 61.50; H, 4.58 (%).

m/e: 196.

EXAMPLE 11

Following the procedure of Example 1, 6-chloro-3,4-dihydro-2H-1-benzopyran-4-one (5.0 g.), trimethylsilyl cyanide (8.0 g.) and zinc iodide (0.50 g.) were reacted to form 6-chloro-4-cyano-4-trimethylsilyloxy-3,4-dihydro-2H-1-benzopyran. Filtration and chromatography over silica gel (80 ml.) eluted with chloroform:hexane (1:1) yielded 7.21 g. of product, m.p. 72°-73° C.

Analytical: Calcd. C, 55.40; H, 5.72; N, 4.97 (%). Found: C, 55.71; H, 5.41; N, 5.09 (%).

EXAMPLE 12

Following the procedure of Example 2, 6-chloro-4-cyano-4-trimethylsilyloxy-3,4-dihydro-2H-1-benzopyran (6.0 g.) and stannous chloride dihydrate (30 g.) were reacted in glacial acetic acid (25 ml.) and concentrated hydrochloric acid (25 ml.) to form 6-chloro-3,4-dihydro-2H-1-benzopyran-4-carboxylic acid. Filtration and chromatography over silica gel (300 ml.) eluted with chloroform:hexane (1:1) yielded 2.91 g. of product, m.p. 90°-90.5° C. (sublimed).

Analytical: Calcd: C, 56.46; H, 4.27 (%). Found: C, 56.31; H, 4.35 (%).

m/e: 212, 214.

EXAMPLE 13

Following the procedure of Example 1, 6-chloro-4H-3,4-dihydro-2H-naphtho[1,2-b]pyran-4-one (4.13 g.), trimethylsilyl cyanide (15 ml.) and zinc iodide (0.75 g.) were reacted in ether (15 ml) to give 6-chloro-4-cyano-4-trimethylsilyloxy-3,4-dihydro-2H-naphtho[1,2-b]pyran. Filtration and chromatography on silica gel (250 ml.) eluted with 1:1 chloroform:hexane yielded 4.7 g. of product.

EXAMPLE 14

Following the procedure of Example 2, 6-chloro-4-cyano-4-trimethylsilyloxy-3,4-dihydro-2H-naphtho[1,2-b]pyran (0.52 g.), stannous chloride dihydrate (1.94 g.) were reacted in glacial acetic acid (5 ml.) and concentrated hydrochloric acid (5 ml.) to form 6-chloro-3,4-dihydro-2H-naphtho[1,2-b]pyran-4-carboxylic acid. Recrystallization from ethyl acetate-hexane yielded 0.23 g. of product, m.p. 141°-142° C.

Analytical: Calcd: C, 64.01; H, 4.22 (%). Found: C, 64.01; H, 4.22 (%).

m/e: 262.

EXAMPLE 15

6-chloro-3,4-dihydro-2H-1-benzothiopyran-4-one (6.8 g.) was combined with trimethylsilyl cyanide (12 ml.) and zinc iodide (0.30 g.) and stirred at room temperature for 72 hours. The reaction mixture was diluted with diethyl ether, washed with saturated sodium bicarbonate and with saturated brine. After drying over magnesium sulfate the solution was filtered and evaporated to dryness under vacuum to give 6-chloro-4-cyano-4-trimethylsilyloxy-3,4-dihydro-2H-1-benzothiopyran (6.0 g., 57%) as an oil.

EXAMPLE 16

Following the procedure of Example 2, 6-chloro-4-cyano-4-trimethylsilyloxy-3,4-dihydro-2H-1-benzothiopyran (5.8 g.) was reacted with stannous chloride dihydrate in glacial acetic acid (25 ml.) and concentrated hydrochloric acid (25 ml.). Recrystallization from benzene:cyclohexane gave 6-chloro-3,4-dihydro-2H-1-benzothiopyran-4-carboxylic acid (2.59 g.), m.p. 153°-154° C.

Analytical: Calcd: C, 52.52; H, 3.97 (%). Found: C, 52.33; H, 3.90 (%).

EXAMPLE 17

In a flame dried flask under nitrogen equipped with a mechanical stirrer, trimethyl phosphonoacetate (10.9 g.) was added dropwise to a slurry of 50% sodium hydride (2.9 g.) in 300 ml. freshly dried tetrahydrofuran and stirred at room temperature for 1 hour. A solution of 6-chloro-3,4-dihydro-2H-1-benzopyran-4-one (10 g.) in 100 ml. of freshly dried tetrahydrofuran was added dropwise, keeping the temperature below 30° C. during the addition. The solution was then heated at reflux for 5 hours and stirred at room temperature for 12 hours. The solution was poured into ice-water, extracted with diethyl ether, washed with water and dried over magnesium suflate. The solution was treated with activated charcoal and evaporated under vacuum to yield a yellow oil (6.3 g.). Chromatography on silica gel (900 ml.) eluted with 1:1 hexane:ethyl acetate yielded 6-chloro-3,4-dihydro-2H-1-benzopyran-4-ylidene-acetic acid methyl ester, (1.6 g., 12%), m.p. 113°–115° C.

EXAMPLE 18

6-chloro-3,4-dihydro-2H-1-benzpyran-4-ylidene-acetic acid methyl ester (2.0 g.) was reduced with hydrogen using a 10% Pd-charcoal catalyst (0.20 g.) by stirring at 25° C. in ethyl acetate for 4 hours. The reduction product, 6-chloro-3,4-dihydro-2H-1-benzopyran-4-acetic acid methyl ester (1.0 g.), was heated for 3 days at reflux temperature with potassium hydroxide (2.4 g.) in 25 ml. water. The solution was acidified and extracted with chloroform. Recrystallization from cyclohexane gave 6-chloro-3,4-dihydro-2H-1-benzopyran-4-acetic acid (650 mg. 60%), m.p. 115°–117° C.

Analytical: (⅛ $C_6H_{12}$. ⅛ $H_2O$): Calcd: C, 58.93; H, 5.36; Cl, 14.80 (%). Found: C, 58.56; H, 5.17; Cl, 14.98 (%). m/e: 226.

EXAMPLE 19

The compounds produced in Examples 2, 4, 6, 8, 10, 12, 14, 16 and 18 were tested for their ability to reduce or inhibit aldose reductase enzyme activity, following the procedure described in U.S. Pat. No. 3,821,383 and based on the procedure of Hayman et. al., Journal of Biological Chemistry, 240, 877 (1965). The substrate employed was partially purified aldose reductase enzyme obtained from calf lens. The results obtained with each compound at a concentration of $10^{-4}M$ are expressed as percent inhibition of enzyme activity.

| Compound of Example | % Inhibition at $10^{-4}M$ |
| --- | --- |
| 2 | 74/67 |
| 4 | 92/76 |
| 6 | 87/89 |
| 8 | 82/89 |
| 10 | 71 |
| 12 | 85/81 |
| 14 | 88/90 |
| 16 | 70 |
| 18 | 69 |

(/ = results of duplicate tests).

EXAMPLE 20

The compounds of Examples 10, 12 and 14 were tested for their ability to reduce or inhibit sorbitol accumulation in the sciatic nerve of streptozotocinized (i.e., diabetic) rats by the procedure essentially described in U.S. Pat. No. 3,821,383. In the present study, the amount of sorbitol accumulation in the sciatic nerves was measured 27 hours after induction of diabetes. The compounds were administered orally at a 25 mg./lg. dosage level at 4, 8 and 24 hours following the administration of streptozotocin. The results obtained in this manner are presented below in terms of percent inhibition (%) afforded by the test compound as compared to the case where no compound was administered (i.e., the untreated animal where sorbitol levels normally rise from approximately 50–100 mM/g. tissue to as high as 400 mM/g. tissue in the 27-hour period):

| Compound of Example | % Inhibition at 25 mg/kg. p.o. t.i.d. |
| --- | --- |
| 10 | 11 |
| 12 | 28 |
| 14 | 12 |

What is claimed is:

1. A compound of the formula

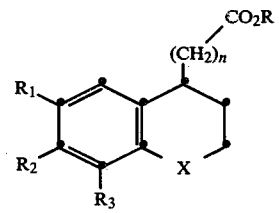

and the pharmaceutically acceptable salts thereof, wherein X is selected from the group consisting of O, S, S=O and

n is zero or one;

R is selected from the group consisting of hydrogen and alkyl of 1 to 4 carbon atoms;

$R_1$ is selected from the group consisting of hydrogen, chloro, bromo, fluoro and phenyl;

$R_2$ and $R_3$, when taken individually, are each selected from hydrogen, alkyl of 1 to 3 carbon atoms, chloro, bromo and fluoro; and when taken together, $R_2$, $R_3$ and the carbon atoms to which they are connected form a fused benzene ring; with the proviso that at least one of $R_1$, $R_2$ and $R_3$ is selected from the group consisting of chloro, bromo and fluoro.

2. A compound of claim 1 wherein X is O.

3. A compound of claim 2 wherein n is zero.

4. A compound of claim 3 wherein $R_1$ is chloro.

5. A compound of claim 4 wherein R is hydrogen.

6. A compound of claim 5 wherein $R_2$ is hydrogen and $R_3$ is methyl.

7. A compound of claim 5 wherein $R_2$ is hydrogen and $R_3$ is chloro.

8. A compound of claim 5 wherein $R_2$ and $R_3$ are each hydrogen.

9. A compound of claim 5 wherein $R_2$, $R_3$ and the carbon atoms to which they are connected form a fused benzene ring.

10. A compound of claim 3 wherein $R_1$ is phenyl.

11. A compound of claim 10 wherein R is hydrogen.

12. A compound of claim 11 wherein $R_2$ is hydrogen and $R_3$ is chloro.

13. A compound of claim 3 wherein $R_1$ is fluoro.

14. A compound of claim 13 wherein R, $R_2$ and $R_3$ are each hydrogen.

15. A compound of claim 2 wherein n is one.

16. A compound of claim 15 wherein $R_1$ is chloro.

17. A compound of claim 16 wherein R, $R_2$ and $R_3$ are each hydrogen.

18. A compound of claim 1 wherein X is S.

19. A compound of claim 18 wherein n is zero.

20. A compound of claim 19 wherein $R_1$ is chloro.

21. A compound of claim 20 wherein R is hydrogen.

22. A compound of claim 21 wherein $R_2$ is chloro and $R_3$ is hydrogen.

23. A compound of claim 21 wherein $R_2$ and $R_3$ are each hydrogen.

24. A pharmaceutical composition comprising a pharmaceutically acceptable carrier and a compound of claim 1 in an amount effective for the treatment of diabetic cataracts, neuropathy or retinopathy.

25. A method of treating a diabetic host for diabetic cataracts, neuropathy or retinopathy which comprises administering to said host an effective amount of a compound of claim 1.

* * * * *